(12) United States Patent
Moskowitz et al.

(10) Patent No.: US 11,458,280 B2
(45) Date of Patent: *Oct. 4, 2022

(54) APPARATUS AND METHOD FOR FACILITATING COGNITIVE CLARITY VIA COLOR PALETTE TRANSITIONS IN A VIRTUAL SKY PROJECTED IN A DIGITAL SPACE WITH A GAZE POINT EXPERIENCING CYCLICAL SIZE CHANGES

(71) Applicant: Synapcis Inc., Los Angeles, CA (US)

(72) Inventors: Michael H. Moskowitz, Mill Valley, CA (US); Glen West, Los Angeles, CA (US)

(73) Assignee: Synapcis Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/672,610

(22) Filed: Feb. 15, 2022

(65) Prior Publication Data

US 2022/0241546 A1  Aug. 4, 2022

Related U.S. Application Data

(63) Continuation-in-part of application No. 17/354,337, filed on Jun. 22, 2021, now Pat. No. 11,266,808.

(Continued)

(51) Int. Cl.
*A61M 21/02* (2006.01)
*G02B 27/18* (2006.01)
*A61M 21/00* (2006.01)

(52) U.S. Cl.
CPC .............. *A61M 21/02* (2013.01); *G02B 27/18* (2013.01); *A61M 2021/005* (2013.01);
(Continued)

(58) Field of Classification Search
CPC .......... A61M 21/02; A61M 2021/0022; A61M 2021/0027; A61M 2021/005;
(Continued)

(56) References Cited

U.S. PATENT DOCUMENTS 3,919,787 A * 11/1975 Bessho ................. G09B 27/06
434/286
10,565,777 B2 * 2/2020 Mallinson ............... G06T 19/20
(Continued)

FOREIGN PATENT DOCUMENTS

EP 3098628 A1 * 11/2016
WO WO-2016145064 A1 * 9/2016

*Primary Examiner* — Michael Le
(74) *Attorney, Agent, or Firm* — Cooley LLP (57) ABSTRACT

A method includes projecting a dark virtual sky in a digital space. The dark virtual sky is transitioned to a dawn virtual sky in the digital space. The dawn virtual sky is altered to introduce a daytime virtual sky in the digital space. The daytime virtual sky is modified to produce a dusk virtual sky in the digital space. These operations are performed via color palette transitions in the virtual sky in the digital space in a time period of less than six minutes. The color palette transitions are in proportional time segments of a twenty-four hour day punctuated by periods of light and darkness of variable length corresponding to the revolution of the earth around the sun. A gaze point is formed in the digital space. The gaze point experiences size changes between a minimum size and a maximum size during a gaze point size change cycle. The gaze point size change cycle is repeated throughout the time period of less than six minutes.

18 Claims, 3 Drawing Sheets

Related U.S. Application Data

(60) Provisional application No. 63/144,898, filed on Feb. 2, 2021.

(52) U.S. Cl.
CPC .............. *A61M 2021/0022* (2013.01); *A61M 2021/0027* (2013.01); *A61M 2205/507* (2013.01)

(58) Field of Classification Search
CPC .. A61M 2205/507; G02B 27/18; G06T 19/00; G06T 3/40
See application file for complete search history.

(56) References Cited

U.S. PATENT DOCUMENTS

| | | | | |
|---|---|---|---|---|
| 2007/0109311 | A1* | 5/2007 | Suda | G06T 15/04 345/582 |
| 2014/0111637 | A1* | 4/2014 | Zhang | B60R 1/088 348/118 |
| 2015/0084520 | A1* | 3/2015 | Reed | H05B 47/16 315/152 |
| 2015/0102749 | A1* | 4/2015 | Soler | A61N 5/0618 315/307 |
| 2018/0043130 | A1* | 2/2018 | Moore-Ede | A61M 21/0094 |
| 2018/0350144 | A1* | 12/2018 | Rathod | G06T 13/40 |
| 2018/0361109 | A1* | 12/2018 | Eng | G06F 3/147 |
| 2020/0289321 | A1* | 9/2020 | Luo | A61B 5/4812 |

\* cited by examiner

APPARATUS AND METHOD FOR FACILITATING COGNITIVE CLARITY VIA COLOR PALETTE TRANSITIONS IN A VIRTUAL SKY PROJECTED IN A DIGITAL SPACE WITH A GAZE POINT EXPERIENCING CYCLICAL SIZE CHANGES

CROSS-REFERENCE TO RELATED APPLICATION

This application is a continuation-in-part of U.S. Ser. No. 17/354,337, filed Jun. 22, 2021, which claims priority to U.S. Provisional Patent Application Ser. No. 63/144,898, filed Feb. 2, 2021, the contents of each application are incorporated herein by reference.

FIELD OF THE INVENTION

This invention relates generally to alleviating symptoms stemming from a disrupted circadian rhythm. More particularly, this invention is directed toward techniques for resetting a circadian rhythm via color palette transitions in a virtual sky projected in a digital space.

BACKGROUND OF THE INVENTION

A circadian rhythm is a process that regulates the sleep-wake cycle associated with a 24-hour period (reference to a 24-hour period includes slightly longer solar and sidereal days). Air travel and excessive work commonly disrupt an individual's circadian rhythm and subsequently leads to physical disorders, such as fatigue, anxiety and depression.

Thus, there is a need to address the problem of disrupted circadian rhythms.

SUMMARY OF THE INVENTION

A method includes projecting a dark virtual sky in a digital space. The dark virtual sky is transitioned to a dawn virtual sky in the digital space. The dawn virtual sky is altered to introduce a daytime virtual sky in the digital space. The daytime virtual sky is modified to produce a dusk virtual sky in the digital space. These operations are performed via color palette transitions in the virtual sky in the digital space in a time period of less than six minutes. The color palette transitions are in proportional time segments of a twenty-four hour day punctuated by periods of light and darkness of variable length corresponding to the revolution of the earth around the sun. A gaze point is formed in the digital space. The gaze point experiences size changes between a minimum size and a maximum size during a gaze point size change cycle. The gaze point size change cycle is repeated throughout the time period of less than six minutes.

BRIEF DESCRIPTION OF THE FIGURES

The invention is more fully appreciated in connection with the following detailed description taken in conjunction with the accompanying drawings, in which.

Like reference numerals refer to corresponding parts throughout the several views of the drawings.

DETAILED DESCRIPTION OF THE INVENTION

Figure 1:
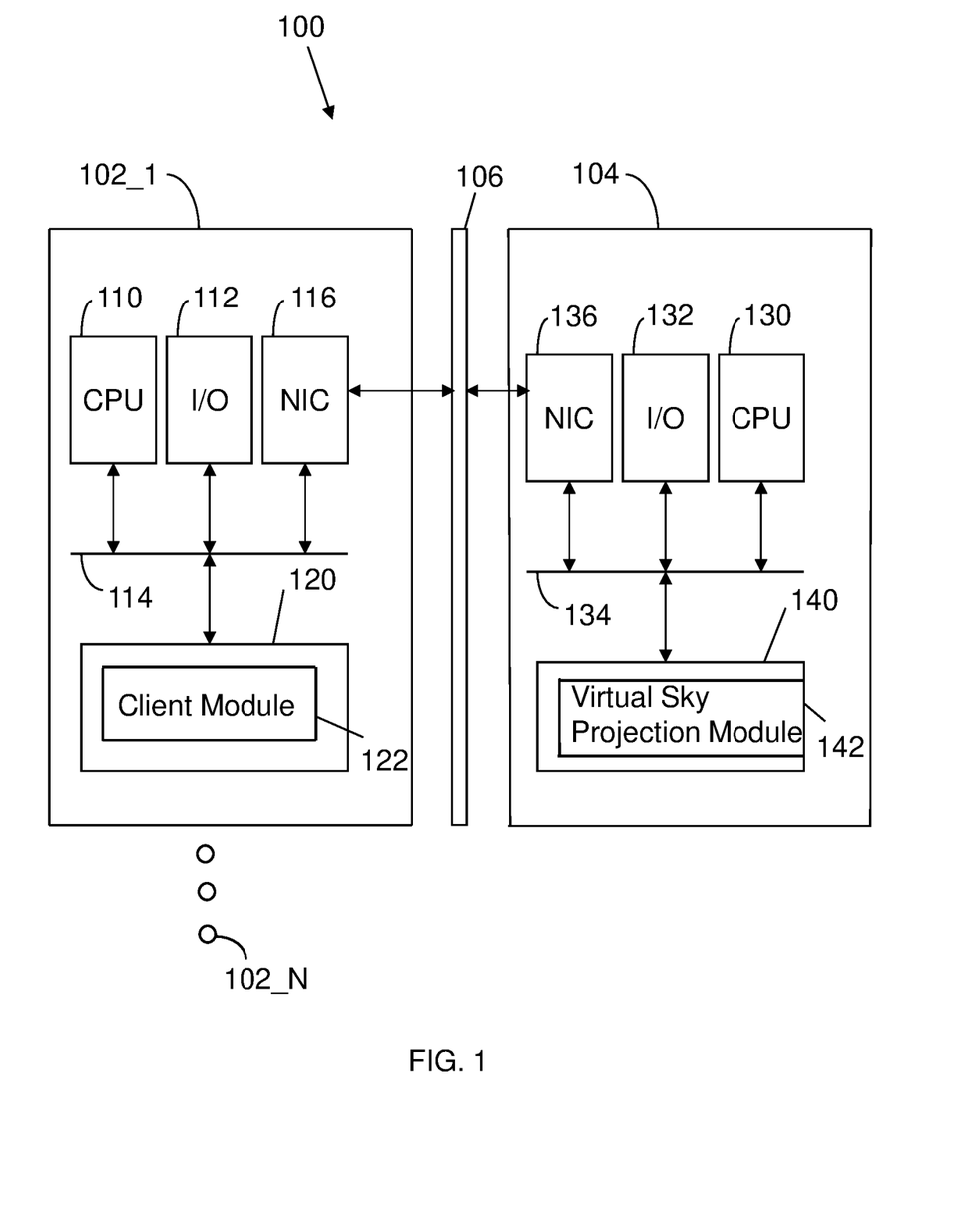
FIG. 1 illustrates a system configured in accordance with an embodiment of the invention.

FIG. 1 illustrates a system 100 configured in accordance with an embodiment of the invention. The system 100 includes a set of client devices 102_1 through 102_N in communication with a server 104 via a network 106, which may be any combination of wired and wireless networks. The client devices 102_1 through 102_N may be computers, tablets, mobile devices, game consoles, game controllers, head-mounted devices and the like. By way of example, client device 102_1 includes a processor 110 (e.g., a central processing unit) in communication with input/output devices 112 via a bus 114. The input/output devices 112 may include input devices, such as a keyboard, mouse, touch display and the like. The output devices include at least one display, which may be circular. The output devices may include multiple display devices. The output devices may be head-mounted devices. A network interface circuit 116 is also connected to bus 114 to provide connectivity to network 106. A memory 120 is also connected to the bus 114. The memory 120 stores a client module 122 with instructions executed by processor 110 to access server 104 to obtain digital content of the type disclosed herein. The digital content is displayed to a user on one or more output devices.

Server 104 includes a processor 130, input/output devices 132, bus 134 and network interface circuit 136. A memory 140 is connected to bus 134. The memory 140 stores a virtual sky projection module 142 with instructions executed by processor 130 to implement operations disclosed herein. The virtual sky projection module 142 may be installed on any one of client devices 102_1 through 102_N. The invention is disclosed in the context of a client-server environment by way of example, not by way of limitation.

Figure 2:
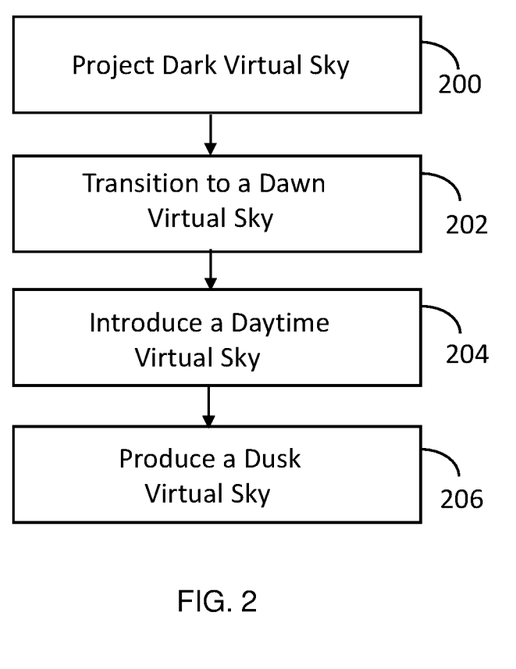
FIG. 2 illustrates processing operations associated with an embodiment of the invention.
Figure 3A:
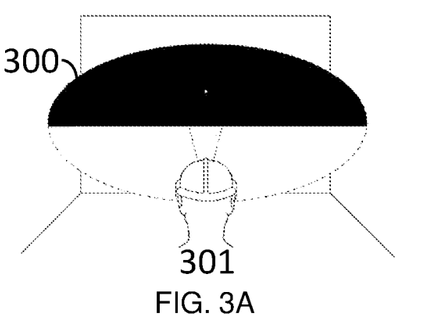
FIG. 3 illustrates transitions in a virtual sky projected in digital space in accordance with an embodiment of the invention.

FIG. 2 illustrates operations implemented by the virtual sky projection module 142. A dark virtual sky is projected in digital space 200. FIG. 3A illustrates a dark virtual sky 300 presented to a subject 301. In one embodiment, the dark virtual sky includes one or more gaze point objects. In this example, there is a single gaze point object in the form of a light circle in the dark virtual sky. The dark virtual sky may be on a display, a set of displays, a circular display, the walls of an enclosed space, a head-mounted device and the like.

Figure 3B:
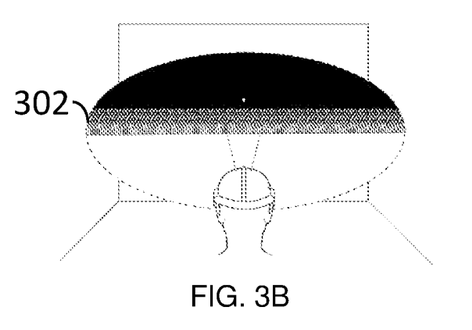

The next operation of FIG. 2 is to transition to a dawn virtual sky 202. FIG. 3B illustrates a dawn virtual sky 302. A pre-dawn virtual sky may proceed the dawn virtual sky in the digital space.

Figure 3C:
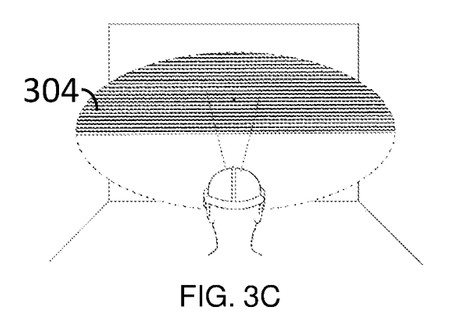

The next operation of FIG. 2 is to introduce a daytime virtual sky 204. FIG. 3C illustrates a daytime virtual sky 304.

Figure 3D:
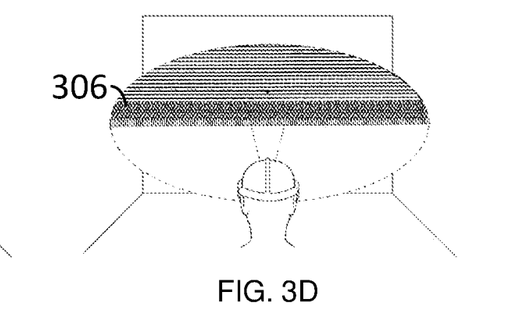

The final operation of FIG. 2 is to produce a dusk virtual sky 206. FIG. 3D illustrates a dusk virtual sky 306. A pre-dusk virtual sky may proceed the dusk virtual sky in the digital space.

The invention is fully disclosed. The following discussion supplies additional details associated with various embodiments of the invention.

In one embodiment, there is provided a function on a display unit or as projected onto or through a surface which functions as a display unit, a singular object or plurality of objects (i.e., gaze point object or gaze point objects), at a fixed point or bounded by a region or moving or rotating in two or three-dimensional space, realized at a distance from the user as part of a horizon or above a ground plane in a virtual representation or simulacrum of the earth's sky. The projection of the virtual sky may be equirectangular or panoramic or wide, upon which the user gazes while their full field of view is enveloped by an ever-changing transition of color gradation and light intensity occurring at an increased speed. This transformation imitates the variance in sky colors and their brightness during the passage of a twenty-four-hour day-night cycle. In one embodiment, this occurs without graphical representations of planetary bodies (e.g., sun, moon, stars) present in the virtual sky.

The user experiences in a full field of view the constantly developing appearance of the earth's sky between sunrise and sunset and nighttime, realized in a virtual environment and across a compressed time period, rather than in real time. The compressed time is from an hour to mere seconds or other user-definable duration. In one embodiment, the compressed time period is six minutes or less. In so doing, the Invention mimics the transforming color temperature of the earth's sky from OK to <7000K and solar irradiance from 0 w/m$^2$ to 1250 w/m$^2$, and the effects of diffuse sky radiation such as Rayleigh and Ramen scattering of sunlight, and meteorological changes such as temperature inversion, that turn the sky a multitude of colors over a twenty-four hour period with shifting lambency: from the blue colors of the daytime and twilight sky, to the burning red and yellow hues of dusk, as well as other optical phenomena such as green flashes.

By exposing the user to the dynamic color palette of a virtual sky with an accelerated day-night cycle, the disclosed technology coordinates chronosynchronization throughout body systems, resetting to their initial temporal state physiological functions affected by dysregulation and/or asynchronism: autonomous oscillations, known as circadian rhythms, in and relative to the suprachiasmatic nucleus of the hypothalamus and the body's network of organ, tissue, and cells which prevent or alleviate the effects of autonomic dysfunction, acute fatigue and myalgic encephalomyelitis (chronic fatigue), anxiety and depression.

The process of establishing chronosynchronization in the user is independent of environment setting and requires that the user participate in an activity which focusses gaze at a fixed point, relative to the user, while the transition of hues and brightness fills, envelops or occurs in their field-of-view. The transition has a variable graphical appearance which triggers the user's cognitive recognition of night and day or other light patterns affecting cognitive perception. The location, shape or appearance, size, position, orientation and, if moving on a trajectory, speed of transit or rotation and direction of the object(s), may be varied, whether by the user or dynamically.

The virtual sky can be displayed in a standalone environment or, where embedded, can dynamically interact with the flow of an environment, such as in a game program or the real world. The user can voluntarily summon the virtual sky or be prompted to do so if a computer program determines that the user needs to reset the autonomous oscillations of the body, whether as according to a predetermined condition or a condition generated by the computer or program itself. User interaction with the virtual sky may include button, gesture or voice commands.

A variation of the technology is its ability to establish chronosynchronization using a day-night cycle relative to the user's latitude and/or longitude, whereupon the color gradation and light intensity will reflect the real-world sky at the user's geographic location.

A variation of the technology is its ability to establish chronosynchronization by imitating a day-night cycle relative to that of another planetary object and its geostationary or geosynchronous orbit. Color temperature and solar irradiance, or other optical phenomena, in the real-world sky on another planetary object may be sampled or calculated using, including but not limited to, photographs and video captured by an autonomous exploration vehicle and subsequently reproduced in the virtual sky.

An embodiment of the technology is a display to the user when a portable head-mounted electronic device or apparatus is worn on the user's head, such as a virtual reality or augmented reality or mixed reality head-mounted device, or other such device or apparatus which may or may not retain a portable electronic device as a method of operation and communication, but which otherwise acts as a method of display to the user.

Another embodiment of the technology is its representation not only on a singular display surface but also across multiple display surfaces such as a computer, portable display screen, folding device with or without flexible display screen, mobile phone, watch, seatback or wall-mounted display, augmented reality head-up display, digital mirror device, or holographic display. Irrespective of the proximity from the user, the user may hold, place or situate in front of themselves a singular display or multiple displays while looking at and interacting with the virtual sky. Interactions with the virtual sky may include by capacitive touch, eye tracking or any other method of interaction determined by the user and/or software and/or device, which either partially or in its entirety can span multiple screens and/or devices and is platform agnostic.

An embodiment of the technology is its representation in a spacecraft, space station and/or other orbital station and/or permanent infrastructure sustaining human operations on another planet and/or other astronomical body, aircraft and/or motor vehicle and/or train and/or tram and/or boat, not only on a singular display surface but also across multiple display surfaces such as a computer, portable display screen, seatback or wall-mounted display, augmented reality head-up display, digital mirror device or holographic display.

An embodiment of the technology is its representation in any environment, such as a bedroom, clinic or office, the interior of a vehicle, or an art gallery installation space, wherein a single lighting device or multiple lighting devices, whether smart lighting devices or not, and whether controlled by a smart lighting control system or not, emit(s) or project(s) a color temperature and light transition in the surrounding area whereupon a person's gaze may be fixed at any point, whether directed to or not.

The disclosed technology coordinates a process of chronosynchronization in a person's circadian system by resetting circadian rhythms to their default state throughout the network of organ, tissue, cells and free-living, nonphotosynthetic prokaryotes in the human body. The disclosed technology, therefore, facilitates precise temporal organization of cellular processes through the stabilization of cellular clocks, further regulating stochastic timing in gene expression as part of the overall circadian system.

It is the way of all living things that life is born, matures, ages and dies. Humans are temporal by our very nature, having associated the measurement of time with a twenty-four hour day, punctuated by periods of light and darkness of variable length, with the revolution of the earth as it, in turn, revolves around the sun. Consequently, our bodies use time to keep us alive and functioning for every cell in the body possesses a circadian clock. As these cells organize into tissues, which further organize into organs, they all tell time. There is a rate, rhythm, sequence and timing to everything which has to be coordinated, and this function is performed by the suprachiasmatic nucleus of the hypothalamus.

The suprachiasmatic nucleus coordinates organs, tissues and cells in a top down manner, synchronizing everything a human being does that involves time, just as the cells, tissues and organs inform the suprachiasmatic nucleus about what needs to be coordinated. At the same time varied rhythms and frequencies in the body must be independently run by the organs, such as a person's heartbeat and differences in systolic and diastolic pressure, while still fitting in the overall scheme of the suprachiasmatic nucleus's coordination. These rhythms are affected primarily by light and dark cycles, but also by more independently controlled variables such as sleep length, sleep timing, artificial light, eating times, etc.

As society industrialized in the Victorian age and took control of the environment, so people learned to abolish the dark with various forms of artificial light which impeded their sleep by entraining the circadian system to both delay the onset of sleep and shorten its duration. People let factors other than the appearance of dawn wake them to go to work and early-night moonlight to send them to their slumber and now perform their work around the clock instead of during traditional daylight hours.

These environmental factors and activities, among many others, throw off circadian rhythms in the body which affect people in profound ways. It is universally accepted that these circadian rhythm disturbances interfere with sleep, but they also affect everything in our bodies that involves timing, sequencing, rhythms, oscillations and rates, i.e. everything that keeps a person alive and functioning. Injuries, illnesses, psychological trauma and aging all affect the complex network of circadian rhythms, thereby causing dysfunction, dysregulation or asynchronism. As this begins, so inflammation and cellular breakdown occurs, thus resulting in serious illnesses such as dysautonomia, cancer, diseases of aging, depression, seasonal affective disorder, endocrine disease, acute fatigue and myalgic encephalomyelitis (chronic fatigue), heart disease, addiction, sleep disturbance and cognitive problem solving deficits, alongside a broad set of additional symptoms. It is the circadian system's ability to coordinate all of the body's timing mechanisms that determines when people start to malfunction, down to the cellular level. As this system breaks down and stops functioning, we die, whether from a catastrophic injury or a slow, lingering illness. Regardless of the cause, when the circadian rhythm system ceases to function, life can no longer be supported.

The disclosed technology addresses the effects of sleep disorders by exposing the user to a transition of color temperature and light intensity that reproduces or pertains to the time period between the onset of dusk and the emergence of dawn in a day-night cycle. The disclosed technology should be used during hours of darkness to establish chronosynchronization, prior to or after a waking, during which time the user may experience disorders of: initiating and maintaining sleep, excessive somnolence, a sleep-wake schedule disruption, and other dysfunctions associated with sleep, sleep stages, or partial arousals including parasomnias. People who experience sleep-wake schedule disruptions, owing to an irregular or compressed sleep schedule in response to their working environment, will benefit from chronosynchronization being established by the disclosed technology, including but not limited to: night-shift workers, military personnel and defense contractors, professional athletes, long-haul goods transportation drivers, miners, and scientists and researchers working in extreme conditions such as at the earth's poles.

The disclosed technology further addresses the effects of asynchronism in the circadian system as a direct consequence of jet or travel lag and space flight, orbit and exploration. In jet or travel lag, asynchronism in the circadian system occurs as the result of a person being exposed to temporary shifts in the day-night cycle while traveling across time zones. Transient disruption to sleep architecture causes phase misalignments of the sleep-wake cycle which are addressed by use of the disclosed technology to establish chronosynchronization at the geographic point of departure and subsequent point of arrival. In space travel, orbit and exploration, asynchronism occurs in the circadian system as people enter into a different day-night cycle to earth. Be it in space flight or while stationary or geostationary, the circadian system is subjected to the rotation of a planetary object. On the international space station, astronauts experience an entire day-night cycle rotating around the earth once every ninety minutes. Space lag is, therefore, extreme, causing substantive disruption to sleep architecture. To address this issue, it is critical that a day-night structure be maintained in space which mirrors that on earth. The invention does this by establishing chronosynchronization relative to earth's day-night cycle. However, the invention can also display a day-night cycle relative to that of another planetary object, where this different time period may be deemed necessary for chronosynchronization to be achieved in space flight towards the planetary object, or upon the planetary surface.

The circadian system in the human body will inevitably fail. Its long-lasting stability is remarkable, however it will break down with aging, injury, chronic illness and trauma. The circadian system is dependent upon external factors affecting the hypothalamus and the cellular clocks. In a virtual or projected environment these variables can be taken into account and coordinated in a significantly compressed timespan. Conversely, real world attempts to reset the cellular clocks within the circadian system are fraught with failure, with accepted clinical medical practice being: (1) light and dark exposure, including specific bands of light with or without cognitive behavioral therapy; (2) pharmaceutical intervention; (3) the rotation of a person's sleep patterns, such that they time their sleep schedule three hours ahead on a daily basis until arriving at a desired hour some seven to eight days later; and (4) a combination of the above mentioned light and dark exposure, feeding and fasting behavior and physical exercise, which requires that the individual make significant lifestyle changes. Unlike these minimally effective approaches, that can take years to see results, embodiments of the invention take minutes to perform a reset of the circadian system, which can be repeated at timed intervals with no impact on lifestyle.

Further, in virtual, augmented or mixed reality, time, timing, sequence, rate, rhythm, oscillation, brain wave entrainment including alpha, beta, delta, gamma, theta and other waves, light, dark, color, latitude, longitude, season, can all be configured and brought to bear both concurrently and at the user's convenience. In normal reality, the precision of this approach would not be possible. The goal, therefore, is to instruct the circadian system to reset itself at the suprachiasmatic nucleus and for that reset to then be channeled among the cellular clocks. As genes turn other genes on and off, so the circadian system makes granular adjustments to a person's innate sense of time that can have a lasting and cumulative effect. Instead of taking days to years to attempt to reset, this can be done in as little as a minute and as long as six minutes. Further, as the circadian clock in every cell is adjustable by systemic and local machinations of the sympathetic (systemic) and parasympathetic (local) nervous systems, demonstrable outputs can be seen from those automatic activities in the human body which do not require conscious intervention; those which are sequenced and timed by the circadian rhythms that determine cortisol release sequencing, dopamine release amount, location sequencing, light to dark sequencing, and blood brain barrier sequencing.

Once adjustments are made at genetic levels, so instruction sets are sent out within the human body to modify the circadian system. This involves adjustment at the suprachiasmatic nucleus, instructing entrainment downwards as the cellular clocks further instruct entrainment upwards to it. In concert with daily resets at morning and bedtime, in our modern environments that inhibit natural circadian rhythms which are set at dawn and dusk, the changes should not only occur but should last. By resetting the overall circadian system we may slow down the effect of time on our bodies. Indeed, it is not the passage of time that creates problems, rather it is asynchronism of these autonomous oscillations that does; it is the failure to lock circadian rhythms to the cellular clocks that causes inflammation which subsequently ages us.

Resetting the circadian system at rise and bedtime should establish a stable entrainment that does not drift in time as much. When it does, use of the disclosed technology should reset the asynchrony, thereby preventing or inhibiting further temporal drift which will cause more circadian clock disruptions over time. Since each organ relies upon its specific use of time, that must remain coordinated by light and dark periods being received by the retina and passed to the suprachiasmatic nucleus, sequential daily resets should also be soothing and relaxing, imparting energy during the day and restful sleep at night, while further maintaining good melatonin levels and fighting off major illnesses.

A good illustration of circadian entrainment is the sequencing people do during the day. We tend to perform many steps in a specific order to get through the day. If that sequencing is disrupted, however, we tend to experience mild discomfort which is only corrected by putting subsequent steps back in order. If that discomfort is allowed to build, anxiety develops. Therefore, coordinating the sequences with the drifting circadian system restores well-being. Resetting the circadian system regularly should decrease anxiety substantively.

Since resetting the circadian rhythm system is so difficult in real time in the real world, no one has ever really had the chance to study this effect in people over time. Using the disclosed technology allows us to do so simply, quickly, and effectively. Further, developing a routine of using the disclosed technology upon awakening and going to sleep should afford people a great hedge against diseases of aging and slow down aging itself. Clearly, the circadian system has direct effects upon epigenetics and, if used regularly, the invention could positively alter the epigenome.

The virtual sky can be varied or altered while accomplishing its objective as the activity involved is unrelated to the end result. The user can be instructed to perform actions that have little to do with the end result or otherwise perform actions without being aware of the end result. There is a wide scope to vary the representation of the technology by changing color, intensity, texture, dimension, shape, sound, flavor and smell. It is also not necessary to represent the color temperature and light intensity transition as mimicking the day-night cycle. In addition, sound alone may be used to assist with some aspects of entrainment of the circadian system, affording visually-impaired users access to the invention.

Different methods of directing user attention or engagement and activity can also be applied to the invention, whether dynamically or not, by varying the appearance of the singular object or plurality of objects as well as the point of engagement and the method of engagement. User engagement activities can include pointing, gesturing and glancing, and user instruction can be varied (e.g. "look ahead and shoot the ball."). Embodiments of the invention can be accessed through a variety of software or hardware devices and be augmented by a range of observations through the application of machine learning and artificial intelligence, as well as neural interfacing and processing tools.

A variation of the technology is the ability to scale or transform a singular object or plurality of objects at a fixed point upon which the user gazes by numerically increasing in size the object(s) height, width and depth dimensions over a timed duration and numerically decreasing in size the object(s) height, width and depth dimensions over a further timed duration. Whereupon a plurality of objects are visible to the user, the dimensions of these individual objects may be numerically augmented or diminished in size independently of each other and the timed duration of the scaling of their dimensions may also occur independently. The singular object or plurality of objects may be rotated at any angle or velocity. The process of resizing a singular object or plurality of objects over timed durations gives rise to a synesthetic experience. By replacing an auditory rhythm that the user hears by means of an auditory input in the region of 0.01 Hz up to 1 kHz, at an optimal range of 0.01-400 Hz, with a visual rhythm received and transmitted by the user's visual cortex, an oscillation is set up between the Default Mode Network (DMN) and Frontoinsula Network (FIN) brain regions that establishes an entrainment of these two brain super-networks. A variation of the invention is the ability to scale or transform a singular object or plurality of objects at a fixed point upon which the user gazes by changing the form of the singular object or plurality of objects over a timed duration. The singular object or plurality of objects may also be transformed to their original form over an additional timed duration. The singular object or plurality of objects may be rotated at any angle or velocity.

Embodiments of the invention replace one sensation (e.g., visual) for another (e.g., auditory or vibratory). Other embodiments augment one sensation with another. In the visual realm, it is known that visual patterns at or around 17 Hz risk visually induced seizures. Accordingly, embodiments of the invention avoid visualizations proximate to this value. Thus, for example, an auditory input or a vibratory input may be transformed into a visual input that oscillates between 0.01 Hz to 12 Hz. As another example, an auditory input or a vibratory input may be transformed into a visual input that oscillates above 24 Hz. In another embodiment, a visual input is transformed into or augmented with an auditory input or a vibratory input in the range of 0.01 Hz to 400 Hz.

As previously discussed, an embodiment of the invention includes a gaze point in the digital space, as shown in FIGS. 3A-3D. Cyclical size changes of the gaze point may be used for facilitating cognitive clarity. In particular, the virtual sky projection module 142 augments the operations of FIG. 2 to include cyclical size changes of a gaze point, as outlined below.

A gaze point is formed in the digital space. The gaze point experiences size changes between a minimum size and a maximum size during a gaze point size change cycle, where the gaze point size change cycle is repeated throughout the time period of the user experience. In one embodiment, the minimum size is a unit size and the maximum size is twelve times the unit size. In another embodiment, the maximum size is four times the unit size. In one embodiment, the unit size is approximately 2 mm in the digital space.

In certain embodiments, the gaze point size change cycle is between ten and thirty seconds. In one embodiment, the gaze point size change cycle is twenty seconds. As shown in FIGS. 3A-3D, the gaze point changes visibility characteristics depending upon current color palette transitions in the virtual sky in the digital space. In one embodiment, the gaze point cyclical size changes are coordinated with visual or vibratory phenomena at approximately 0.05 Hz.

It is well established that cognitive function is on a continuum. Variations in cognitive function occur because of illness, natural aging processes, developmental phases of life and daily vicissitudes. Normal cognitive function is dependent on in-phase circadian rhythms. However, when these circadian rhythms fall out-of-phase, individuals will experience symptoms of cognitive dysfunction known as "brain fog." There is a need to facilitate cognitive clarity to overcome such brain fog.

Normal function of the circadian rhythm is critical to managing the Blood Brain Barrier. During a day period of a day-night cycle, light exposure determines molecular ingress into the brain by opening the Blood Brain Barrier to transport substances from the body to the brain via the unique capillary system of the central nervous system. This allows for brain nutrition and energy consumption. During a night period of a day-night cycle, and in direct contrast to a day period, the circadian rhythm reverses the flow of substances to the body from the brain, thereby removing residual and retained biological waste material, the consequence of normal brain metabolism and a major contributor to cognitive defects. To stabilize cognitive dysfunction, it is necessary to create a delta wave stimulus in the periventricular area that activates the glymphatic system to reverse the blood-brain barrier.

The user experiences color palette transitions in a virtual sky for an experience period (e.g., six minutes or less). The user enters the virtual experience at their current time and completes a twenty-four hour day-night cycle within the experience period. The color palette transitions in the experience period are as described above, such that the experience incorporates color palette transitions from dawn to daytime to dusk to night, as well as color temperature and intensity changes.

The user gazes at a fixed point object above the horizon that oscillates in a sinusoidal pattern (e.g., at 0.05 Hz per cycle of twenty seconds). In one embodiment, the size and perspective of the fixed point object increases for half of the duration of the sinusoidal waveform, e.g., 10 seconds, and then decreases in size and perspective for the remaining half duration of the sinusoidal waveform, e.g., 10 seconds. This gives the user the impression that the fixed point object is expanding into the foreground and receding into the distance every cycle. This oscillation remains constant throughout the experience period.

The invention stabilizes and manages the in-phase circadian rhythm to promote deep-delta sleep and reversal of the Blood Brain Barrier, thereby optimizing appropriate performance of removal of waste material from the brain and central nervous system. The invention utilizes the circadian rhythm day-night cycle mimicking a 24-hour period in a collapsed experience period of six minutes or less. Embodiments of the invention use synesthetic substitutions, whether vibratory, visual, or auditory, to create synergistic responses that manage the in-phase circadian rhythm. By replacing an electrical input at 0.05 Hz in the brain with a visual rhythm of 0.05 Hz received and transmitted by the user's visual cortex, an oscillation is set up that instructs the Blood Brain Barrier to form channels into which the ventricles of the brain empty cerebral spinal fluid. The fluid rushes through the channels at sixteen times the normal velocity of cerebral spinal fluid in the brain. The pressure created by the velocity of cerebral spinal fluid in these channels consequently forces waste material, carried with it from the rest of the brain, out into the body's systemic circulation through the pervasive tight junctions of the brain's capillary walls.

If a person's circadian rhythm is in-phase, the waste material ejection process utilizing cerebral spinal fluid normally takes place during deep-delta sleep on a daily basis. When this is not the case, waste removal is inefficient and contributes to cognitive deficits colloquially identified as brain fog.

An embodiment of the present invention relates to a computer storage product with a computer readable storage medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs, DVDs and holographic devices; magneto-optical media; and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using JAVA®, C++, or other object-oriented programming language and development tools. Another embodiment of the invention may be implemented in hard-wired circuitry in place of, or in combination with, machine-executable software instructions.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A method, comprising:
   projecting a dark virtual sky in a digital space;

transitioning the dark virtual sky to a dawn virtual sky in the digital space;

altering the dawn virtual sky to introduce a daytime virtual sky in the digital space;

modifying the daytime virtual sky to produce a dusk virtual sky in the digital space, wherein projecting, transitioning, altering and modifying are performed via color palette transitions in the virtual sky in the digital space in a time period of less than six minutes, wherein the color palette transitions are in proportional time segments of a twenty-four hour day punctuated by periods of light and darkness of variable length corresponding to the revolution of the earth around the sun; and forming a gaze point in the digital space, the gaze point experiencing size changes between a minimum size and a maximum size during a gaze point size change cycle, where the gaze point size change cycle is repeated throughout the time period of less than six minutes.

2. The method of claim 1 wherein the minimum size is a unit size and the maximum size is twelve times the unit size.

3. The method of claim 2 wherein the maximum size is four times the unit size.

4. The method of claim 3 wherein the unit size is approximately 2 mm in the digital space.

5. The method of claim 1 wherein the gaze point size change cycle is between ten and thirty seconds.

6. The method of claim 5 wherein the gaze point size change cycle is twenty seconds.

7. The method of claim 1 wherein the gaze point changes visibility characteristics depending upon current color palette transitions in the virtual sky in the digital space.

8. The method of claim 1 further comprising presenting sound in the range of 0.01 Hz to 1 kHz.

9. The method of claim 8 further comprising presenting sound in the range of 0.01 Hz to 400 Hz.

10. The method of claim 1 further comprising presenting vibrations at approximately 0.05 Hz.

11. The method of claim 1 further comprising transforming an auditory input or a vibratory input into a visual input that oscillates between 0.01 Hz to 12 Hz.

12. The method of claim 1 further comprising transforming an auditory input or a vibratory input into a visual input that oscillates above 24 Hz.

13. The method of claim 1 further comprising transforming visual input into an auditory input or a vibratory input in the range of 0.01 Hz to 400 Hz.

14. The method of claim 1 implemented on a head-mounted device.

15. The method of claim 1 implemented on multiple display devices.

16. The method of claim 1 implemented on a circular display device.

17. The method of claim 1 wherein the digital space is two-dimensional.

18. The method of claim 1 wherein the digital space is three-dimensional.

* * * * *